US008648005B2

(12) United States Patent
Sakamoto et al.

(10) Patent No.: US 8,648,005 B2
(45) Date of Patent: Feb. 11, 2014

(54) METHOD FOR PREPARING CATALYST

(75) Inventors: Toru Sakamoto, Wakayama (JP); Shoji Hasegawa, Wakayama (JP)

(73) Assignee: Kao Corporation, Tokyo (JP)

( * ) Notice: Subject to any disclaimer, the term of this patent is extended or adjusted under 35 U.S.C. 154(b) by 287 days.

(21) Appl. No.: 13/063,246

(22) PCT Filed: Sep. 10, 2009

(86) PCT No.: PCT/JP2009/066202
§ 371 (c)(1),
(2), (4) Date: Mar. 10, 2011

(87) PCT Pub. No.: WO2010/030037
PCT Pub. Date: Mar. 18, 2010

(65) Prior Publication Data
US 2011/0166393 A1 Jul. 7, 2011

(30) Foreign Application Priority Data
Sep. 11, 2008 (JP) ................................ 2008-233586

(51) Int. Cl.
*B01J 23/00* (2006.01)
*B01J 23/72* (2006.01)
*B01J 23/02* (2006.01)
*B01J 23/06* (2006.01)
*B01J 23/70* (2006.01)
*C07C 51/36* (2006.01)
*C07C 31/18* (2006.01)
*C07C 27/00* (2006.01)
*C07C 29/00* (2006.01)

(52) U.S. Cl.
USPC ........... 502/318; 502/319; 502/331; 502/343; 502/345; 502/346; 554/141; 554/146; 568/852; 568/861

(58) Field of Classification Search
USPC ................. 502/318, 319, 331, 343, 345, 346; 554/141, 146; 568/852, 861
See application file for complete search history.

(56) References Cited

U.S. PATENT DOCUMENTS

| | | | |
|---|---|---|---|
| 3,197,418 A * | 7/1965 | Maebashi et al. ............. | 502/244 |
| 4,758,546 A | 7/1988 | Baer et al. | |
| 4,808,562 A | 2/1989 | Kubersky et al. | |
| 4,918,248 A * | 4/1990 | Hattori et al. ................. | 568/885 |
| 5,008,235 A * | 4/1991 | Wegman et al. .............. | 502/342 |
| 5,229,346 A | 7/1993 | Mori et al. | |
| 5,334,779 A * | 8/1994 | Kuo ............................... | 568/864 |
| 5,481,048 A | 1/1996 | Tsukada et al. | |
| 5,554,574 A * | 9/1996 | Tsukada et al. ............... | 502/345 |
| 5,658,843 A | 8/1997 | Tsukada et al. | |
| 6,410,806 B2 * | 6/2002 | Oku et al. ..................... | 568/814 |
| 6,495,706 B2 * | 12/2002 | Aoki et al. .................... | 554/146 |
| 8,188,321 B2 * | 5/2012 | Suzuki et al. ................. | 568/861 |
| 8,258,351 B2 * | 9/2012 | Suzuki et al. ................. | 568/852 |
| 2001/0016671 A1 | 8/2001 | Oku et al. | |

FOREIGN PATENT DOCUMENTS

| | | |
|---|---|---|
| CN | 1107756 A | 9/1995 |
| CN | 1116412 A | 2/1996 |
| JP | 61-161146 A | 7/1986 |
| JP | 62-14945 A | 1/1987 |
| JP | 5-177140 A | 7/1993 |
| JP | 7-163880 A | 6/1995 |
| JP | 10-245351 A | 9/1998 |
| JP | 2990568 B2 | 12/1999 |
| JP | 2000-93800 A | 4/2000 |
| JP | 2001-199917 A | 7/2001 |
| JP | 3195357 B2 | 8/2001 |
| JP | 2006-16332 A | 1/2006 |
| JP | 2008-132475 A | 6/2008 |

OTHER PUBLICATIONS

Notification of First Office Action for corresponding Chinese Patent Application No. 200980135737.1, dated Nov. 13, 2012.
International Search Report, dated Jan. 12, 2010, issued in PCT/JP2009/066202.

* cited by examiner

*Primary Examiner* — Patricia L Hailey
(74) *Attorney, Agent, or Firm* — Birch, Stewart, Kolasch & Birch, LLP

(57) ABSTRACT

The present invention provides a method of preparing the copper-containing hydrogenation catalyst having high activity by liquid phase reduction without decreasing purity of the solvent and a method for efficiently producing an alcohol. The present invention provides the method of preparing the copper-containing hydrogenation catalyst, including reducing a molded precursor of the copper-containing hydrogenation catalyst by supplying hydrogen gas or a mixture of hydrogen gas with an inert gas at a temperature of 50 to 150° C. in the presence of a solvent to obtain the copper-containing hydrogenation catalyst, wherein the reduction is conducted at an average reduction velocity of the copper-containing hydrogenation catalyst of not more than 3.0% by weight/hour. The present invention also provides the method of producing an alcohol, including preparing the copper-containing hydrogenation catalyst by the method of preparation, and subjecting a carboxylic acid or a carboxylic acid ester to catalytic reduction with hydrogen in the presence of the prepared copper-containing hydrogenation catalyst.

11 Claims, No Drawings

US 8,648,005 B2

METHOD FOR PREPARING CATALYST

FIELD OF THE INVENTION

The present invention relates to a method for preparing a copper-containing hydrogenation catalyst and a method for producing an alcohol.

BACKGROUND OF THE INVENTION

For producing alcohols including aliphatic, alicyclic or aromatic alcohols by hydrogenation of carboxylic acids or carboxylates, there have been many methods disclosed from the 1930s onward. In hydrogenation of carboxylates, particularly of fatty acid esters, use of copper-based catalysts has been mainly proposed.

Conditions for reductive activation of these catalysts are determined according to a form in use, a method of use, a mode of reaction, and the like. For example, in a fixed-bed reaction system, a molded catalyst is entirely subjected to gas phase reduction for activation. In industry, such reduction of a catalyst is generally carefully conducted at a predetermined temperature under an inert gas flow that contains several to several tens percent of hydrogen in order to avoid local overheat due to rapid reduction of the catalyst. For instance, JP-A 61-161146 describes disadvantage of such gas phase reductive activation of a catalyst concerned with productivity of an alcohol as taking a time from 4 to 14 days.

As described above, fixed-bed reaction systems generally employ gas phase reduction, but some systems employ liquid phase reduction to activate a copper-containing catalyst precursor. For example, JP-B 2990568 discloses liquid phase reduction of a molded precursor of a copper-containing hydrogenation catalyst, that reduction is conducted at a temperature ranging from 50 to 140° C. According to this method, a copper-containing hydrogenation catalyst can be prepared that has significantly improved catalytic activity and selectivity compared with that prepared by gas phase reduction. However, in Examples and Comparative Examples of JP-B 2990568, a catalyst prepared in Example 1 in which reduction is conducted at 130° C. and a catalyst in Comparative Example 2 in which reduction is conducted at 200° C. are almost similar to each other in selectivity. Comparative Example 2, however, has a high catalytic activity by about 10% than Example 1. The reason of necessity of the upper limit of a reduction temperature in spite of an increased catalytic activity by reduction at higher temperature is as follows. As described in paragraphs 0010 and 0011 of JP-B 2990568, liquid phase reduction conducted at too high temperature will deactivate a catalyst with water and fatty acid, and will largely decrease a purity of a solvent with ester wax and hydrocarbons, that by-products are generated during a reduction treatment.

In order to increase catalytic activity and selectivity, JP-B 3195357 discloses a two-step reduction of a molded precursor of a copper-containing hydrogenation catalyst, including a first step of reducing the precursor in a liquid phase at 20 to 140° C. such that at least 10% by weight of copper oxide is reduced at a point of reaching to 140° C. and then a second step of further reducing the precursor in a liquid phase at 140 to 250° C. As described in Examples and Comparative Examples of JP-B 3195357, catalysts prepared in Examples had relative activities 1.2 to 1.5 times higher than that of a catalyst prepared by gas phase reduction in Comparative Example 1, which clearly shows an advantage of the disclosed liquid phase reduction. However, in any of these Examples and Comparative Examples, a reduction temperature was finally increased to 170 to 200° C., suggesting decrease of purity of a solvent.

SUMMARY OF THE INVENTION

The present invention provides a method for preparing a copper-containing hydrogenation catalyst, including reducing a molded precursor of the copper-containing hydrogenation catalyst by supplying hydrogen gas or a mixture of hydrogen gas with an inert gas at a temperature of 50 to 150° C. in the presence of a solvent to obtain the copper-containing hydrogenation catalyst, wherein the reduction is conducted at an average reduction velocity of the copper-containing hydrogenation catalyst of not more than 3.0% by weight/hour.

The present invention provides a method for producing an alcohol, including preparing a copper-containing hydrogenation catalyst by the method described above, and then subjecting a carboxylic acid or a carboxylic acid ester to catalytic reduction with hydrogen in the presence of the prepared copper-containing hydrogenation catalyst.

The present invention provides use of a copper-containing hydrogenation catalyst prepared by the method described above to produce an alcohol by subjecting a carboxylic acid or a carboxylic acid ester to catalytic reduction with hydrogen.

DETAILED DESCRIPTION OF THE INVENTION

As described above, considering with deterioration of a solvent, conventional methods cannot increase a reduction temperature, or cannot prepare a catalyst having high activity.

As described above, in conventional liquid phase reduction, there is no reduction method of preparing a catalyst having high activity without decreasing purity of a solvent.

The present invention provides a method for preparing a copper-containing hydrogenation catalyst having high activity without decreasing purity of a solvent by liquid phase reduction and an efficient method for producing an alcohol.

According to the method of the present invention, a copper-containing hydrogenation catalyst having high activity can be prepared without decreasing purity of a solvent. The copper-containing hydrogenation catalyst prepared by the method of the present invention has a long catalyst life and can produce an alcohol with high quality at low cost, which is very advantageous in industrial production.

[Preparation of a Copper-Containing Hydrogenation Catalyst]

Examples of a precursor of the copper-containing hydrogenation catalyst used in the present invention include, but not specifically limited to, copper-chromium oxides, copper-zinc oxides, copper-iron oxides, copper-aluminum oxides and copper-silica oxides. These precursors may be used alone or in combination of two or more. Among these precursors of the copper-containing hydrogenation catalyst, preferred are copper-zinc oxides. Specific examples include CuO—ZnO—[an oxide of at least one metal selected from the group consisting of elements of groups IIa and IIIb of the Periodic Table, lanthanide and actinide] described in paragraphs 0013 to 0014 of JP-A 5-177140.

A content of copper oxide in the total weight of the precursor of the copper-containing hydrogenation catalyst used in the present invention is preferably 5 to 98% by weight, and more preferably 20 to 98% by weight. The precursors of the copper-containing hydrogenation catalyst may be supported on a carrier such as a silica, an alumina, a zirconium oxide, a titanium oxide, and a silica-alumina carriers. In this case, the total weight of the precursor of the copper-containing hydrogenation catalyst refers a weight including such carriers.

In the present invention, a molded precursor of the copper-containing hydrogenation catalyst is used. A shape of the molded precursor can be arbitrary selected within the scope that does not interfere with an operation of a fixed-bed reactor. In general, the molded catalyst used preferably has a cylindrical shape produced by tableting or extrusion molding or a spherical particle shape having a size of 1 to 20 mm, because the catalyst having such a shape can be easily produced at low cost.

In the present invention, the precursor of the copper-containing hydrogenation catalyst is reduced by supplying hydrogen gas or a mixture of hydrogen gas with an inert gas in the presence of a solvent. The solvent used in the reduction preferably substantially does not cause elution or irreversible adsorption of copper oxide or metal copper and formation of a compound with copper, and preferably has low concentration of catalyst poisons such as nitrogen compounds/sulfur compounds/phosphor compounds. The solvent used is in the liquid state under the treatment conditions of reductive activation of the catalyst. Preferred are glyceride oils, esters, alcohols, and hydrocarbons. More preferred are glyceride oils, fatty acid esters, aliphatic alcohols, and hydrocarbons, that do not affect adversely on quality of a produced alcohol in production of the alcohol of the main purpose of the present invention. These solvents may be used alone or in combination of two or more. Specific examples of the glyceride oil include mono-, di- and triglycerides constructed with fatty acids having 6 to 22 carbon atoms. Examples of the fatty acid esters include esters of fatty acids having at least one or more fatty acid group having 2 to 22 carbon atoms with aliphatic alcohols having 1 to 22 carbon atoms. Examples of the aliphatic alcohols include those having 2 to 22 carbon atoms and at least one hydroxy group and presenting in the liquid state under the conditions of reductive activation. Examples of the hydrocarbons include liquid paraffin and cyclic hydrocarbons.

Other solvent may be used as long as residual impurity derived from the solvent does not affect seriously on quality of a produced alcohol. Examples of such a solvent include ethers, aldehydes, and ketones, that are in the liquid state under the conditions of reductive activation of the catalyst. In these organic compounds, including the esters and the alcohols, an alkyl group includes at least any one of a linear chain, a branched chain, an aliphatic ring and an aromatic ring.

From the viewpoints of achieving a uniform wet state of the catalyst with the solvent and preventing partial reduction of the catalyst in a gas phase, in the present invention, a flow rate of the solvent is preferably not less than 0.1 $[Hr^{-1}]$ of a liquid hourly space velocity. From the economic viewpoint, the flow rate is preferably not more than 5.0 $[Hr^{-1}]$, and more preferably not more than 3.0 $[Hr^{-1}]$.

In the method of the present invention, as a reductant, hydrogen gas or a mixture of hydrogen gas with an inert gas is used. Examples of the inert gas used herein include nitrogen, helium, argon, and methane gases. Use of the inert gas enables control of a hydrogen concentration in the mixed gas to control a reduction velocity. Further, dilution effect of hydrogen concentration by the inert gas prevents rapid progress of reduction near an inlet to a catalyst layer at an initial stage of the reduction, resulting in more effective production of a catalyst having high activity, which is an advantage of the liquid phase reduction. From the viewpoint of productivity, a concentration of hydrogen in the mixed gas is preferably not less than 2% by volume, more preferably not less than 10% by volume, even more preferably not less than 20% by volume, and even more preferably not less than 25% by volume. From the viewpoint of increasing activity of a produced catalyst, the concentration is preferably not more than 100% by volume, more preferably not more than 95% by volume, even more preferably not more than 90% by volume, even more preferably not more than 80% by volume, and even more preferably not more than 60% by volume. Considering a time taking to the reductive activation, a concentration of hydrogen is desirably set such that a hydrogen partial pressure is not less than one atmosphere.

Supply of a gas is preferably conducted under a pressure condition of an ambient pressure to 30 MPa (300 atmospheres) in the presence of a solvent. Although the effects of the present invention can be achieved under a pressure over 30 MPa, such a condition puts heavy load on facilities. From the economic viewpoint, the pressure condition is preferably not more than 30 MPa.

From the viewpoint of providing good heat-removing effect and effective reduction of water produced in reduction to achieve sufficient catalytic properties, supply of a gas is preferably a gas hourly space velocity of not less than 30 $[Hr^{-1}]$, and more preferably not less than 50 $[Hr^{-1}]$. From the viewpoint of facilities, a gas hourly space velocity is preferably not more than 10000 $[Hr^{-1}]$, and more preferably not more than 5000 $[Hr^{-1}]$.

In general, temperatures of introducing a solvent to an inlet of a catalyst layer and of introducing a gas are preferably 20 to 60° C. in order to start the reduction of a catalyst under conditions as mild as possible. A temperature of the catalyst is then increased to a temperature of the reductive activation. In the present invention, from the viewpoint of achieving sufficient velocity of catalyst reduction, a temperature of the reductive activation is preferably not lower than 50° C., more preferably not lower than 60° C., and even more preferably not lower than 80° C. From the viewpoint of preventing a solvent such as an ester and an alcohol from quality deterioration, the temperature is preferably not higher than 150° C., more preferably not higher than 140° C., and even more preferably not higher than 130° C. For example, when the reductive activation is conducted in an alcohol as a solvent at a temperature not higher than 150° C., by-products such as wax esters and aldehydes are not produced, and there is not so large problem as decrease of alcohol purity.

As used herein, the temperature of the reductive activation refers a temperature that substantially most contributes to the liquid phase reduction. For example, in order to start reduction of a catalyst under conditions as mild as possible, a solvent, hydrogen gas and the like are introduced at 20 to 60° C. and heated, as described above. During this heating step, the reductive activation progresses a little. However, the reductive activation progresses mainly in the temperature range of 50 to 150° C. For example, when a reaction system is hold at 130° C. for a given time to progress the reaction, it refers that the liquid phase reduction is performed at 130° C.

The liquid phase reduction of the catalyst precursor may be performed principally at a constant temperature, or during increasing a temperature, or under conditions including both states. Increasing of the temperature may be continuous or discontinuous, and an increasing rate of temperature needs not to be constant. It is without any problems that the liquid phase reduction thus can be performed either at a constant temperature or with changed increasing rates in the way. In the present invention, a reduction rate of catalyst and an average reduction velocity are determined as follows.

reduction rate=total amount of water produced by reduction/theoretical amount of water produced by reduction of a catalyst precursor [% by weight]

average reduction velocity=100% by weight of reduction water/time taking to the reduction [% by weight/hour]

time taking to the reduction=time from the start of increasing a temperature to the end of the reduction As used herein, a theoretical amount of water produced by reduction of a catalyst precursor refers a total amount of reduction water produced when all metal oxides in the catalyst precursor are reduced to metals.

An amount of water produced by reduction can be determined by measuring a concentration of water in a solvent at an inlet and an outlet of a reactor over time by a known measuring method such as the Karl-Fischer method and calculating a difference. In the present invention, a point that an amount of water produced by reduction reaches to not more than 0.1% by weight is considered as the end of the reduction. A total amount of water from the start of a reduction operation to the end of the reduction is considered as a total amount of water produced by the reduction. Data of a reduction rate over time thus obtained can be used to calculate a reduction velocity at a certain interval and an average reduction velocity from the start to the end of the reduction. In the present invention, the reduction conducted at an average reduction velocity of not more than 3.0% by weight/hour can produce a copper-containing hydrogenation catalyst having high activity even at a relative low temperature as not decreasing purity of a solvent. From the viewpoint of high activity of the copper-containing hydrogenation catalyst, the average reduction velocity is more preferably not more than 2.5% by weight/hour, even more preferably not more than 2.2% by weight/hour, and even more preferably not more than 2.0% by weight/hour. The lower limit of the average reduction velocity is not specifically limited. However, too low velocity prolongs an operation of the reduction, which is not economic from the viewpoints of maintaining high temperature facilities and increasing amount of a solvent used. In addition, if a large amount of solvent is used, a trace amount of ingredients in the solvent may affect an active point to decrease an activity of the catalyst. From the viewpoints described above, the average reduction velocity is preferably not less than 0.5% by weight/hour, more preferably not less than 0.8% by weight/hour, even more preferably not less than 1.0% by weight/hour, and even more preferably not less than 1.2% by weight/hour.

In reduction of a catalyst containing copper, one mole of copper oxide generates 20 kcal of reduction heat. Thus, in a pilot-scale or a full-scale equipment including a catalyst layer having a catalyst volume of not less than 1 m$^3$, a temperature of reductive activation in the catalyst layer easily becomes nonuniform. Since reduced copper has extremely low thermal stability, a local temperature of reductive activation in the catalyst layer is also important. From the viewpoint of preparing a catalyst having high activity, in reduction of a molded precursor of the copper-containing hydrogenation catalyst, a reduction velocity is preferably controlled to not more than 3.0% by weight/hour with monitoring a reduction rate of the catalyst during a reduction process. In order to prevent deterioration of properties of the catalyst due to rapid progress of the reduction and/or accumulation of heat, a temperature difference between an inlet of the catalyst layer and an outlet of the catalyst layer is preferably controlled to not more than 40° C., more preferably not more than 30° C., and even more preferably not more than 20° C.

As described above, a reduction velocity can be controlled by detecting an amount of water produced by reduction, or a moisture content at the outlet of the catalyst layer and regulating one or two or more of operational factors selected from a gas flow rate at the inlet of the catalyst layer, a concentration of hydrogen gas at the inlet of the catalyst layer, a temperature of a gas at the inlet of the catalyst layer, an amount of a solvent, a temperature of the solvent, and a temperature of a jacket of a reduction apparatus. Among these factors, a temperature of a gas at the inlet of the catalyst layer is preferably regulated to control the reduction velocity, from the viewpoints of a simple operation and responsibility.

In the method of the present invention, from the viewpoint of sufficient progress of reductive activation, a time of the liquid phase reduction, which may be varied according to conditions such as a temperature and a hydrogen partial pressure described above, is preferably not less than 30 hours, more preferably not less than 40 hours, and even more preferably not less than 50 hours. From the economic viewpoint, the time is preferably not more than 130 hours.

In the present invention, from the viewpoint of preventing elongation of the time taking to conduct reductive activation step of the catalyst precursor, an increasing rate of temperature is preferably not less than 0.5° C./Hr, more preferably not less than 1° C./Hr, and even more preferably not less than 5° C./Hr. From the viewpoint of preventing rapid increase of a temperature due to accumulation of reduction heat accompanied with rapid reduction of the catalyst to easily control the reduction, the increasing rate is preferably not more than 40° C./Hr, more preferably not more than 30° C./Hr, and even more preferably not more than 20° C./Hr.

The copper-containing hydrogenation catalyst prepared by the method of the present invention can be used in a fixed bed continuous reaction process mainly to produce an alcohol and to conduct various hydrogenations such as hydrogenation of an aldehyde or ketone group, hydrogenation of olefins, and hydrogenation of a nitro group. As thus, the liquid phase reduction of the precursor of the copper-containing hydrogenation catalyst is preferably conducted in a reactor for a fixed bed continuous reaction, because the resultant activated catalyst can be used as is to an intended use such as production of an alcohol.

[Method for Producing an Alcohol]

The method of producing an alcohol of the present invention includes subjecting a carboxylic acid or a carboxylic ester to catalytic reduction with hydrogen in the presence of the copper-containing hydrogenation catalyst prepared by the method of the present invention as described above.

Examples of the carboxylic acid of a raw material include natural animal and vegetable fatty acids obtained from coconut oil, palm kernel oil, palm oil, beef tallow, lard and the like and synthesizing fatty acids. Examples of the organocarboxylic acid ester desirably include esters of oil-and-fat and fatty acids. Examples of the oil-and-fat include mono-, di- and triglycerides composed of saturated and unsaturated fatty acids having 6 to 22 carbon atoms. Examples of the fatty acid ester include linear, branched or unsaturated fatty acid esters having at least one carbon atom and at least one ester group. Examples of the fatty acid ester include formates, acetates, caproates, caprylates, caprates, undecenoates, laurates, myristates, palmitates, stearates, isostearates, oleates, arachates, behenates, oxalates, maleates, adipates, and sebacates. An alcohol group that constitutes the fatty acid ester is not limited, but preferably constructed with an aliphatic alcohol having 1 to 22 carbon atoms. An ester to be subjected to hydrogenation in the present invention is not limited to the fatty acid ester, and may be, without any problems, selected from alicyclic carboxylic acid esters, such as cyclohexanecarboxylates, benzoates and phthalates, and aromatic carboxylates and derivatives thereof.

In the present invention, for hydrogenating the organocarboxylic acid or the organocarboxylic acid ester, a fixed-bed continuous reaction process is preferably employed. Hydrogenation can be conducted in a solvent, but desirably without a solvent, considering productivity. When a solvent is used, it is selected from those that do not affect the reaction, including alcohols, dioxanes and paraffins. A reaction temperature is preferably 130 to 300° C., and more preferably 160 to 250° C. A reaction pressure is preferably 0.0098 to 29 MPa (0.1 to 300 kg/cm$^2$). A liquid hourly space velocity in supplying a raw material, which is appropriately determined according to reaction conditions, is preferably within the range of 0.2 to 5.0 [Hr$^{-1}$], considering productivity or reactivity.

EXAMPLES

The following Examples demonstrate the present invention. Examples are intended to illustrate the present invention and not to limit the present invention.

Example 1

According to a method described in Example 5 of JP-A 5-177140, a catalyst precursor containing CuO, ZnO, and BaO supported on TiO$_2$. The resultant precursor powder was formed into a cylindrical tablet and baked for two hours at 400° C. to give a molded precursor of catalyst having a diameter of 3 mm and a height of 3 mm and the following composition by weight:

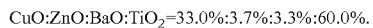

CuO:ZnO:BaO:TiO$_2$=33.0%:3.7%:3.3%:60.0%.

500 cc of the molded precursor of catalyst thus obtained was filled in a fixed bed high-pressure flow reactor, and then used to conduct liquid phase reduction as follows. Under a temperature of 40 to 50° C. and, a mixed gas containing hydrogen and nitrogen at concentrations of 27% by volume and 73% by volume respectively was introduced at a gas flow rate of 75 NL/Hr, and then lauryl alcohol (Kao Corporation, trade name: KALCOL-20, purity: 99.8%) was passed through the reactor at a flow rate of 250 cc/Hr. After flow rates of the liquid and the gas were stabilized, a temperature of the reactor was increased at a rate of 10° C./Hr to 130° C., which was a reduction temperature, under a pressure of 20 kg/cm$^2$ (gauge pressure), and then hold at a steady temperature. Moisture contents in the solvent at an inlet and an outlet of the reactor were measured over time by the Karl-Fischer method. When an amount of water produced by reduction was decreased to 0.1% by weight or less, the reduction was considered as ended. A time taking from the start of increasing a temperature to the end of the reduction, or a reduction time was 60 hours. An average reduction velocity was 1.7% by weight/hour.

After ended reductive activation of the catalyst precursor, lauryl alcohol was changed to fatty acid methyl ester (saponification value: 244) having a distribution of chain length of 8 to 18 carbon atoms. Under conditions of a reaction temperature of 230° C., a reaction pressure of 200 kg/cm$^2$, a liquid hourly space velocity of 1.0 (Hr$^{-1}$), and a flow rate of hydrogen of 25 times by mole to fatty acid methyl ester, hydrogenation was conducted. A decreasing rate of purity of lauryl alcohol collected at the end of reductive activation of the catalyst precursor was determined by a gas chromatograph. The rate was not more than 0.1%. A catalytic activity was determined as a first-order rate constant for the reaction per unit volume of the molded catalyst. The results are shown in Table 1.

In Example 1, the catalyst having high catalytic activity can be prepared without decreasing purity of the solvent, and an alcohol can be efficiently produced with the catalyst. Further, the alcohol produced by hydrogenation had high quality.

Comparative Example 1

A molded precursor of catalyst as described in Example 1 was filled in a fixed bed high pressure flow reactor according to the method described in Example 1, and then subjected to reductive activation in a gas phase for 157 hours at 130° C. with hydrogen diluted in nitrogen gas at a concentration of 1.3 to 5.0% by volume under a pressure of 15 kg/cm$^3$ (gauge pressure) at a gas hourly space velocity of 250 (Hr$^1$) of a mixed gas of nitrogen/hydrogen. The activated catalyst thus obtained was used to hydrogenation of fatty acid methyl ester according to the conditions described in Example 1. The results are shown in Table 1.

In Comparative Example 1, quality of the alcohol produced by hydrogenation was equal to that in Example 1, but productivity of the alcohol was worst due to low activity of the catalyst.

Examples 2 to 4 and Comparative Examples 2 to 3

Catalysts were similarly subjected to reductive activation as in Examples 1 except that some changes in conditions of reductive activation of catalyst were employed as shown in Table 1, and used to produce an alcohol. The results are shown in Table 1.

In Examples 2 to 4, catalysts having high catalytic activity can be prepared without decreasing purity of a solvent. In Comparative Examples 2 to 3, purity of a solvent was decreased, and a catalytic activity was lower than that of Examples. In any of Examples and Comparative Examples, quality of an alcohol produced by hydrogenation was equal to that in Example 1. However, catalysts of Comparative Examples had low catalytic activity, resulting in inferior productivity of alcohol.

Comparative Example 4

A catalyst was similarly subjected to reductive activation as in Examples 1 except that temperature conditions of reductive activation of catalyst were increasing at 10° C./Hr, holding at 140° C. for 30 hours, and then increasing at 10° C./Hr and holding at 200° C. for 6 hours, and used to produce an alcohol. The results are shown in Table 1.

In Comparative Example 4, quality of the alcohol produced by hydrogenation was equal to that of Example 1, but purity of lauryl alcohol collected at the end of reductive activation was decreased, resulting in lower yield.

TABLE 1

|  |  | Example | | | | Comparative example | | | |
| --- | --- | --- | --- | --- | --- | --- | --- | --- | --- |
|  |  | 1 | 2 | 3 | 4 | 1 | 2 | 3 | 4 |
| Conditions of reductive activation of catalyst | | | | | | | | | |
| LHSV*[1] | [Hr$^{-1}$] | 0.5 | 0.5 | 0.5 | 0.5 | — | 0.5 | 0.5 | 0.5 |
| Pressure | [kg/cm$^2$] | 20 | 20 | 20 | 20 | 15 | 20 | 20 | 20 |
| Concentration of hydrogen at an inlet of a catalyst layer | [% by volume] | 27 | 27 | 10 | 50 | 1.3~5.0 | 100 | 100 | 15 |
| Reduction temperature | [° C.] | 130 | 130 | 130 | 130 | 130 | 130 | 200 | 140→200 |
| Reduction time | [hour] | 60 | 53 | 97 | 33 | 157 | 22 | 23 | 52 |
| Average reduction velocity | [% by weight/hour] | 1.7 | 1.9 | 1.0 | 3.0 | 0.6 | 4.5 | 4.4 | 1.9 |
| Catalyst performance | | | | | | | | | |
| Relative activity*[2] | [—] | 195 | 193 | 178 | 148 | 100 | 114 | 124 | 143 |
| Collected solvent | | | | | | | | | |
| Decreasing rate of purity | [%] | <0.1 | <0.1 | <0.1 | 0.3 | — | 1.1 | 8.7 | 10.3 |

*[1]Liquid hourly space velocity of a solvent
*[2]Relative value based on the activity of Comparative Example 1 set to 100

The invention claimed is:

1. A method for preparing a copper-containing hydrogenation catalyst, comprising reducing a molded precursor of the copper-containing hydrogenation catalyst by supplying hydrogen gas or a mixture of hydrogen gas with an inert gas at a temperature of 50 to 150° C. in the presence of a solvent to obtain the copper-containing hydrogenation catalyst, wherein the reduction is conducted at an average reduction velocity of the copper-containing hydrogenation catalyst of not more than 2.5% by weight/hour.

2. The method according to claim 1, wherein the solvent is at least one selected from the group consisting of glyceride oil, fatty acid esters, aliphatic alcohols and hydrocarbons.

3. The method according to claim 1, wherein the precursor of the copper-containing hydrogenation catalyst is at least one oxide selected from the group consisting of copper-chromium oxides, copper-zinc oxides, copper-iron oxides, copper-aluminum oxides and copper-silica oxides.

4. The method according to claim 1, wherein a content of copper oxide is 5 to 98% by weight of the total weight of the precursor of the catalyst.

5. The method according to claim 1, wherein a concentration of hydrogen in a gas used in the reduction is 2 to 95% by volume.

6. The method according to claim 1, wherein an average reduction velocity of the copper-containing hydrogenation catalyst is determined from an amount of water produced by the reduction.

7. A method for producing an alcohol, comprising preparing a copper-containing hydrogenation catalyst by the method according to claim 1, and then subjecting a carboxylic acid or a carboxylic acid ester to catalytic reduction with hydrogen in the presence of the prepared copper-containing hydrogenation catalyst.

8. The method according to claim 1, wherein the reduction is conducted at a temperature-increasing rate of not less than 0.5° C./Hr and not more than 40° C./Hr.

9. The method according to claim 1, wherein the reduction is conducted at the average reduction velocity of not less than 0.5% by weight/hour.

10. A method for preparing a copper-containing hydrogenation catalyst, comprising reducing a molded precursor of the copper-containing hydrogenation catalyst by supplying hydrogen gas or a mixture of hydrogen gas with an inert gas at a temperature of 50 to 150° C. in the presence of a solvent in a reduction apparatus comprising a catalyst layer having an inlet and an outlet in order to obtain the copper-containing hydrogenation catalyst, wherein the reduction is conducted at an average reduction velocity of the copper-containing hydrogenation catalyst of not more than 2.5% by weight/hour;
    wherein a reduction velocity is controlled by regulating one or two or more of operational factors selected from a gas flow rate at the inlet of the catalyst layer, a concentration of hydrogen gas at the inlet of the catalyst layer, a temperature of gas at the inlet of the catalyst layer, an amount of a solvent, a temperature of the solvent and a temperature of a jacket of a reduction apparatus.

11. A method for preparing a copper-containing hydrogenation catalyst, comprising reducing a molded precursor of the copper-containing hydrogenation catalyst by supplying hydrogen gas or a mixture of hydrogen gas with an inert gas at a temperature of 50 to 150° C. in the presence of a solvent in a reduction apparatus comprising a catalyst layer having an inlet and an outlet in order to obtain the copper-containing hydrogenation catalyst, wherein the reduction is conducted at an average reduction velocity of the copper-containing hydrogenation catalyst of not more than 2.5% by weight/hour;
    wherein the reduction is conducted by controlling a temperature difference between the inlet of the catalyst layer and the outlet of the catalyst layer at not more than 40° C.

* * * * *